United States Patent
Beckhaus et al.

(10) Patent No.: US 6,214,762 B1
(45) Date of Patent: Apr. 10, 2001

(54) CATALYSTS BASED ON METAL FULVENE COMPLEXES

(75) Inventors: Rüdiger Beckhaus, Oldenburg; Jürgen Heinrichs, Aachen; Sigurd Becke, Rösrath, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/374,551

(22) Filed: Aug. 13, 1999

(30) Foreign Application Priority Data

Aug. 20, 1998 (DE) .............................. 198 37 734

(51) Int. Cl.$^7$ ............................. B01J 21/00; B01J 21/06; B01J 23/24; B01J 23/16; B01J 27/24
(52) U.S. Cl. ........................ 502/152; 502/150; 502/151; 502/154; 502/162; 502/167; 502/172; 526/160; 526/161; 526/172; 526/943
(58) Field of Search ................... 502/150, 151, 502/154, 162, 167, 172

(56) References Cited

U.S. PATENT DOCUMENTS

| 4,542,199 | 9/1985 | Kaminsky et al. | 526/160 |
|---|---|---|---|
| 4,892,851 | 1/1990 | Ewen et al. | 502/104 |
| 5,026,798 | 6/1991 | Canich | 526/127 |
| 5,132,380 | 7/1992 | Stevens et al. | 526/126 |
| 5,145,819 | 9/1992 | Winter et al. | 502/117 |
| 5,276,208 | 1/1994 | Winter et al. | 556/53 |
| 5,703,187 | 12/1997 | Timmers | 526/282 |

FOREIGN PATENT DOCUMENTS

| 19732804 | 2/1999 | (DE) . |
|---|---|---|
| 0 129 368 | 7/1989 | (EP) . |
| 96/13529 | 5/1996 | (WO) . |

OTHER PUBLICATIONS

J. Am. Chem. Soc. (month unavailable) 1993, 115, pp. 12569–12570.
J. Am. Chem. Soc. (month unavailable) 1994, 116, pp. 8952–8965.
J. Chem. Soc., Chem. Commun. (month unavailable) 1995, pp. 1181–1182.
JACS, Feb. 1972, 94, pp. 1219–1238.
JACS, 110, (month unavailable) 1988, pp. 7701–7715.
Organmetallics, (month unavailable) 1991, pp. 2665–2671.
Organmetallics, (month unavailable) 1991, 10, pp. 1637–1639.
Organmetallics, 1991, vol. 10, pp. 1637–1639, Mar. 1991.*

\* cited by examiner

*Primary Examiner*—Mark L. Bell
*Assistant Examiner*—Michael J. DiVerdi
(74) *Attorney, Agent, or Firm*—Joseph C. Gil; Noland J. Cheung

(57) ABSTRACT

A method of producing metal fulvene insertion complexes, as well as new fulvene metal insertion complexes and the use thereof as catalysts for the polymerization of olefins and/or dienes and as hydrogenation catalysts.

8 Claims, No Drawings

CATALYSTS BASED ON METAL FULVENE COMPLEXES

FIELD OF THE INVENTION

The present invention relates to catalysts based on metal fulvene complexes, to methods of producing them, and to the use thereof for the polymerization and copolymerization of olefins and/or dienes.

BACKGROUND OF THE INVENTION

Since the discovery of ferrocene, metal complexes with cyclopentadienyl ligands have been intensively investigated. The use of biscyclopentadienyl-metal complexes (metallocenes), in admixture with activating co-catalysts, preferably alumoxanes, for the polymerization of olefins and diolefins has long been known (e.g., EP-A 69,951, 129,368, 351,392, 485,821, 485,823). Metallocenes have proven to be highly effective, specific catalysts for the polymerization of olefins. In combination with co-catalysts, metal complexes with only one cyclopentadienyl ligand (semi-sandwich complexes) are also suitable as specific polymerization catalysts (US. Pat. No. 5,132,380, EP 416,815, WO 91/04257, WO 96/13529). There is, therefore, a multiplicity of new metallocene catalysts or semi-sandwich catalysts for the polymerization of olefinic compounds which have been developed in recent years in order to increase catalyst activity and selectivity and to control the microstructure, molecular weights and molecular weight distribution thereof. Metal complexes with cyclopentadienyl ligands, particularly chiral ansa-metallocenes, have also been described as hydrogenation catalysts, e.g., for olefins or imines (J. Am. Chem. Soc. 1993, 115, 12569. J. Am. Chem. Soc. 1994, 116, 8952–8965). Chiral metallocenes are also used as catalysts in asymmetric synthesis, e.g. for asymmetric Diels-Alder reactions (J. Chem. Soc. Chem. Commun. 1995, 1181).

However, relatively little is known about metal complexes with fulvene ligands. According to Bercaw et al., JACS (1972), 94, 1219, the fulvene complex ($\eta^6$-2,3,4,5-tetramethylcyclopentadienyl-1-methylene)($\eta^5$-pentamethylcyclo-pentadienyl)-titanium-methyl is formed by the thermolysis of bis($\eta^5$-pentamethylcyclo-pentadienyl)-titaniumdimethyl.

T. J. Marks et al., JACS (1988), 110, 7701 describes the thermolysis of pentamethylcyclopentadienyl complexes of zirconium and hafnium. The fulvene complex ($\eta^6$-2,3,4,5-tetramethylcyclopentadienyl-1-meth-ylene)($\eta^5$-pentamethylcyclopentadienyl)zirconiumphenyl is formed by the thermolysis of bis($\eta^5$-pentamethylcyclopentadienyl) zirconiumdiphenyl. The production of fulvene complexes by a thermal method is restricted to just a few structural variants. The thermal method does not always result in uniform products.

Metal fulvene complexes and a method of producing them were described in a previous Application (German Patent Application 19 756 742.8). Metal fulvene complexes which cannot be obtained by a thermal method can be obtained in high yield by the reaction of a fulvene compound with a suitable transition metal complex in the presence of a reducing agent. The direct introduction of the fulvene ligand provides access to a multiplicity of fulvene metal complexes. In combination with co-catalysts, specific polymerization catalysts can be produced, the catalytic activity of which is comparable with the activity of catalysts based on metallocenes.

A method of producing metal fulvene complexes by a thermal route, and their use as polymerization catalysts in combination with co-catalysts, is described in the prior Application DE 19 732 804.0.

One disadvantage is that metal fulvene complexes are extremely sensitive to air and moisture. Metal fulvene complexes, therefore, have to be produced and stored under inert gas conditions.

Little is known about the reaction behavior of metal fulvene complexes. The reaction of aldehydes and ketones with the complex compound ($\eta^6$-cyclopentadienyl-1-methylene)($\eta^5$-methylcyclopentadienyl)phenyltitanium is described in Z. Natur-forsch. 44 b, 1989, 1593–1598. The reaction of isonitriles with pentamethylcyclopentadienyltetramethylfulvene complexes of titanium and zirconium is described in Organometallics 1991, 10, 2665–2671. The reaction of ($\eta^6$-2,3,4,5-tetramethylcyclo-pentadienyl-1-methylene)($\eta^5$-pentamethylcyclopentadienyl)titanium chloride with acetophenone is described in Organometallics, 1991, 10, 1637–1639. The reaction products which are formed have not been characterized unambiguously. The reactions described above are restricted to metal fulvene complexes which comprise a cyclopentadienyl ligand in addition and which are produced by a thermal method.

SUMMARY OF THE INVENTION

Nothing is known about the reaction behavior of metal fulvene complexes which are produced by the direct introduction of a fulvene ligand into a metal complex.

The object of the present invention is to identify new catalysts which, at least in part, avoid the disadvantages described above.

Surprisingly, it has been found that new metal fulvene insertion complexes which are superbly suitable as catalysts can be produced by the reaction of metal fulvene complexes with unsaturated compounds which contain one or more hetero atoms.

The present invention relates to a method of producing metal fulvene insertion complexes comprising the step of reacting a) a metal fulvene complex of formula (I)

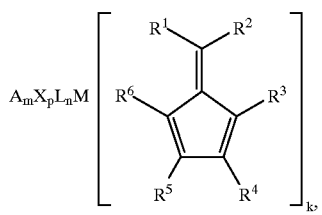

wherein

M is a metal of Groups IIIb, IVb, Vb, VIb or of the lanthanides or of the actinides of the IUPAC periodic table of the elements, A is an anionic ligand which is optionally singly- or multi-bridged, with the exception of cyclopentadienyl ligands, X denotes a hydrogen atom, a $C_1$ to $C_{10}$ alkyl group, a $C_1$ to $C_{10}$ alkoxy group, a $C_6$ to $C_{10}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a silyl group substituted by $C_1$ to $C_{10}$ hydrocarbon radicals, a halogen atom or an amide of formula $NR^7{}_2$, L denotes a neutral ligand, $R^1$, $R^2$, $R^3$, $R^4$, $R^5$, $R^6$ are the same or different and represent hydrogen, a halogen, a cyano group, a $C_1$ to $C_{20}$ alkyl group, a $C_1$ to $C_{10}$ fluoro-alkyl group, a $C_6$ to $C_{10}$ fluoroaryl group, a $C_1$ to $C_{10}$ alkoxy group, a $C_6$ to $C_{20}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_7$ to $C_{40}$ arylalkenyl group, a $C_2$ to $C_{10}$ alkynyl group, a silyl group substituted by $C_1$–$C_{10}$ hydrocarbon radicals, a sulfide group substituted by a $C_1$–$C_{10}$ hydrocarbon radical, or an amino group which is optionally substituted by $C_1$–$C_{20}$ hydrocarbon radicals, or $R^1$, $R^2$, $R^3$, $R^4$, $R^5$, $R^6$ each form one or more aliphatic or aromatic ring systems together with the atoms which bond them, which ring systems may contain one or more hetero atoms (O, N, S) and comprise 5 to 10 carbon atoms, $R^7$ represents hydrogen, a $C_1$ to $C_{20}$ alkyl group, a $C_6$ to $C_{20}$ aryl group, a $C_7$ to $C_{40}$ arylalkyl group, a $C_7$ to $C_{40}$ alkylaryl group, a silyl group which is substituted by $C_1$–$C_{10}$ hydrocarbon radicals, or an amino group which is optionally substituted by $C_1$–$C_{20}$ hydrocarbon radicals, m, p represent the numbers 0, 1, 2, 3 or 4 which result from the valency and the state of bonding of M, k represents the number 1, 2 or 3, and the sum of k+m+p ranges from 1 to 5 depending on the oxidation state of M, and n is a number from 0 to 10, with b) an unsaturated compound of formula (II)

$$R^8{}_aR^9{}_bCY \qquad (II),$$

wherein $R^8$ and $R^9$ are the same or different, and denote a hydrogen atom, a halogen atom, a hydroxy group, a $C_1$ to $C_{10}$ alkyl group, a $C_1$ to $C_{10}$ alkoxy group, a $C_6$ to $C_{10}$ aryl group which is optionally substituted by halogen atoms, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, an amino group which is optionally substituted by $C_1$–$C_{20}$ hydrocarbon radicals, or an imino group which is optionally substituted by $C_1$–$C_{20}$ hydrocarbon radicals, Y denotes a nitrogen atom, an oxygen atom, a sulphur atom or a group of formula $NR^{10}$, wherein $R^{10}$ has the same meaning as $R^8$ and $R^9$, and a and b represent the numbers 0 or 1.

The present invention also relates to metal fulvene insertion complexes which can be produced by this method.

DETAILED DESCRIPTION OF THE INVENTION

The production of the metal fulvene insertion complexes according to the present invention can be illustrated by the following reaction scheme:

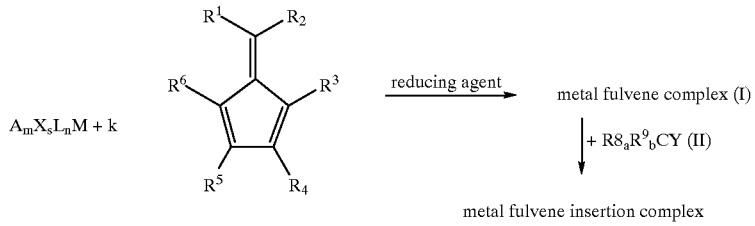

The compounds which are preferably used as unsaturated compounds of formula (II) comprise compounds of formula (IIa):

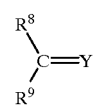

(IIa)

wherein $R^8$, $R^9$ and Y have the meaning given above and $R^8$ and $R^9$ optionally form a ring system, which may contain one or more hetero atoms (O, N, S), with the carbon atom which bonds them, or compounds of formula (IIb),

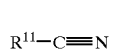

(IIb)

or compounds of formula (IIc),

(IIc)

or compounds of formula (IId)

(IId)

wherin Y represents an oxygen atom or a sulphur atom, and $R^{11}$ denotes a hydrogen atom, a $C_1$ to $C_{10}$ alkyl group, a $C_6$ to $C_{10}$ aryl group which is optionally substituted by halogen atoms, $C_7$ to $C_{40}$ arylalkyl group or a $C_7$ to $C_{40}$ alkylaryl group.

Compounds of formula (IIa) are particularly preferred in which Y represents an oxygen atom and $R^8$ and $R^9$ have the meaning given above. Compounds such as these comprise aldehydes such as formaldehyde, acetaldehyde, propionaldehyde, n-butyraldehyde, isobutyraldehyde, pivalinaldehyde, octanal, octadecenal, acrolein, crotonaldehyde, benzaldehyde or furfural for example, dialdehydes such as glyoxal for example, and ketones, such as acetone, methyl ethyl ketone, diethyl ketone, hexanone-(2), hexanone-(3), methyl tert.-butyl ketone, di-n-propyl ketone, diisopropyl ketone, diisobutyl ketone, di-tert.-butyl ketone, dicyclohexyl ketone, methyl cyclohexyl ketone, diamyl ketone, heptadecyl phenyl ketone, mesitylene oxide, phorone, isophorone, acetophenone, 4-fluoroacetophenone, 3,5-di(trifluoromethyl)acetophenone, pentamethylacetophenone, benzophenone, 4,4'-difluorobenzo-phenone, decafluorobenzophenone, benzal acetone, deoxybenzoin, cyclohexanone, menthone, camphor, and fluorenone for example, and diketones, such as diacetylacetylacetone for example, esters of carboxylic acids, such as ethyl acetate or benzyl benzoate for example.

The preferred compounds of formula (IIb) include nitriles, such as acetonitrile, n-butyronitrile, 4-chlorophenylnitrile, pivalic acid nitrile and cinnamic acid nitrile for example. The preferred compounds of formula (IIc) include isonitriles, such as 2,6-di-methylphenylisonitrile, for example. The preferred compounds of formula (IId) include isocyanates and thioisocyanates, such as cyclohexyl isocyanate and methyl isocyanate for example.

Other preferred compounds of formula (II) include unsaturated compounds of formula (IIa) in which Y denotes a group of formula $NR^{10}$ and $R^8$ and $R^9$ have the meanings given above. Compounds such as these comprise imines, such as acetophenone benzylimine, for example, and hydrazones, such as acetophenone hydrazone, for example.

The process for producing the metal fulvene insertion complexes according to the invention is conducted in a suitable reaction medium at temperatures from –100 to +250° C., preferably from –78 to +130° C., most preferably, from –10 to +60° C.

Examples of suitable reaction media include aliphatic or aromatic hydrocarbons, halogenated hydrocarbons, ethers and cyclic ethers. Particular examples thereof include unbranched aliphatic hydrocarbons such as butane, pentane, hexane, heptane or octane, branched aliphatic hydrocarbons such as isobutane, isopentane or isohexane, cyclic aliphatic hydrocarbons such as cyclohexane or methylcyclohexane, aromatic hydrocarbons such as benzene, toluene and xylene. Ethers such as dialkyl ethers or dimethoxyethane are preferred; tetrahydrofuran is particularly preferred. Mixtures of different solvents are also suitable.

Production of the metal fulvene insertion complexes according to the invention is conducted with the exclusion of air and water under inert conditions (protective gas technique). Examples of inert gases include nitrogen and argon. The Schlenk technique which is generally customary for organometallic substances is suitable as the protective gas technique, for example.

For example, fulvene metal complexes (I) can be produced by the reaction of a transition metal compound of formula (III)

$$A_mX_sL_nM \qquad (III),$$

wherein

A,X,L,M, and n, m and n have the meanings given above, and s denotes the numbers 2, 3, 4, 5 or 6 and s>p, with a fulvene compound of formula (IV)

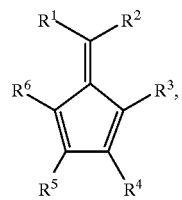

wherein $R^1, R^2, R^3, R^4, R^5$ and $R^6$ have the meanings given above, in the presence of a reducing agent.

Fulvene complexes of formula (I) can be produced in a single reaction step, i.e., in a one-pot reaction, wherein the sequence of adding the individual reaction components is not fixed. The fulvene metal complexes of formula (I) can be isolated and can subsequently be reacted in a separate step with unsaturated compounds of formula (II). The prior isolation of the metal fulvene complexes of formula (I) can also optionally be omitted. The molar ratio of (I) to (II) falls within the range from 100:1 to 0.1:1, preferably from 10:1 to 0.5:1.

Examples of suitable reducing agents include alkali metals, alkaline earth metals, aluminum, zinc, alloys of alkali metals, such as sodium-potassium alloy or sodium amalgam for example, alloys of alkaline earth metals, and metal hydrides. Examples of metal hydrides include lithium hydride, sodium hydride, magnesium hydride, aluminum hydride, lithium aluminum hydride and sodium borohydride. Particular examples of reducing agents include sodium naphthalenide, potassium graphite, lithium alkyls, magnesium butadiene, magnesium anthracene, trialkylaluminum compounds and Grignard reagents. The preferred reducing agents are alkali metals or alkaline earth metals, $C_1$–$C_6$ alkyllithium, tri-$C_1$–$C_6$ alkylaluminum compounds and Grignard reagents, such as, ethylmagnesium chloride for example. The reducing agents which are particularly preferred are lithium, sodium amalgam, magnesium and n-butyl lithium, as well as triethylaluminum and triisobutylaluminum. An electrochemical reduction can also be carried out instead of using the aforementioned reducing agents.

The process for producing metal fulvene complexes (I) is conducted in a suitable reaction medium at temperatures from –100 to +250° C., preferably from –78 to +130° C., most preferably from –10 to +60° C.

Examples of suitable reaction media include aliphatic or aromatic hydrocarbons, halogenated hydrocarbons, ethers and cyclic ethers. Examples thereof include unbranched aliphatic hydrocarbons such as butane, pentane, hexane, heptane or octane, branched aliphatic hydrocarbons such as isobutane, isopentane or isohexane, cyclic aliphatic hydrocarbons such as cyclohexane or methylcyclohexane, aromatic hydrocarbons such as benzene, toluene and xylene. Ethers such as dialkyl ether or dimethoxyethane are preferred; tetrahydrofuran is particularly preferred. Mixtures of different solvents are also suitable.

Production of the catalysts according to the present invention is conducted with the exclusion of air and water under inert gas conditions (protective gas technique). Examples of inert gases include nitrogen and argon. The Schlenk technique which is generally customary for organometallic substances is suitable as the protective gas technique, for example.

Transition metal complexes of formula (III) which are particularly suitable are those in which M is a metal from the group comprising titanium, zirconium, hafnium, vanadium, niobium, tantalum and chromium, A is a pyrazolate of formula $N_2C_3R^{10}{}_3$, wherein $R^{10}$ represents hydrogen, a $C_1$–$C_{10}$ alkyl group or a $C_6$ to $C_{10}$ aryl group;
a pyrazolyl borate of formula $R^7B(N_2C_3R^{10}{}_3)_3$;
an alcoholate or phenolate of formula $OR^7$;
a siloxane of formula $OSiR^7{}_3$;
a thiolate of formula $SR^7$;
an acetylacetonate of formula $(R^7CO)_2CR^7$;
a diimine of formula $(R^7N{=}CR^7)_2$;
an amidinate of formula $R^7C(NR^7{}_2)_2$;
a cyclooctatetraenyl of formula $C_8H_qR^7{}_{8-q}$ where q represents 0, 1, 2, 3, 4, 5, 6 or 7;
wherein
$R^7$ has the meaning given above,
L represents an ether, a thioether, a cyclic ether, a cyclic thioether, an amine or a phosphine, and
X, $R^7$, m, n and S have the meanings given above.

Transition metal complexes of formula (III) are particularly preferred in which

M represents titanium, zirconium or hafnium,

X denotes fluorine, chlorine or bromine,

L denotes diethyl ether or THF, m denotes the number 0, s denotes the numbers 2, 3 or 4, and n is a number from 0 to 4.

Fulvene compounds which are particularly suitable are those of formula (IV) in which $R^1$ to $R^6$ represent a $C_1$–$C_{30}$ alkyl group, a $C_6$–$C_{10}$ aryl group, a $C_7$–$C_{40}$ alkylaryl group, and in particular represent hydrogen, methyl, trifluoromethyl, ethyl, n-propyl, isopropyl, n-butyl, isobutyl, tert.-butyl, phenyl, pentafluorophenyl, methylphenyl, cyclohexyl, benzyl or dimethylamino.

The preferred compounds of formula (IV) are fulvene compounds of formula (V)

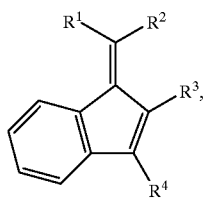

(V)

or fulvene compounds of formula (VI)

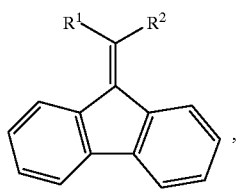

(VI)

wherein $R^1$, $R^2$, $R^3$ and $R^4$ have the meanings given above.

Compounds of formula (IV) which are particularly preferred include 6-cyclohexylfulvene, 6-iso-propylfulvene, 6-tert-butylfulvene, 6-phenylfulvene, 6-(dimethylamino)-fulvene, 6,6-bis(dimethylamino)fulvene, 6,6-dimethylfulvene, 6,6-bis-(tri-fluoromethyl)fulvene, 6,6-diphenylfulvene, 6,6-bis(pentafluorophenyl)fulvene, 6,6-pentamethylenefulvene, 6,6-tetramethylenefulvene, 6,6-trimethylenefulvene 2-(2,4-cyclopentadien-1-yiidene)-1,3-dithiolane, 5-benzylidene-1,2,3-triphenyl-1,3-cyclopentadiene, 1,2,3,4-tetramethyl-fulvene, 1,2,3,4-tetraphenylfulvene, 2,3-dimethyl-fulvene, 2,3-diisopropylfulvene, 2,3-diphenylfulvene, 1,4-dimethyl-2,3-diphenyl-fulvene and 1,4-diethyl-2,3-diphenylfulvene.

The synthesis of fulvene compounds of formulae (IV), (V) and (VI) can be effected, for example, as described in J. Org. Chem., Vol. 49, No. 11 (1984), 1849.

Formula (I) which is given for the metal fulvene complexes should be considered as a formal representation of the bonding relationships, and constitutes one example of a structural variant. The bonding relationships in these metal complexes depend, amongst other factors, on the central atom, on the oxidation state, and on the substituents on the fulvene ligand.

The present invention further relates to the use of these fulvenemetal insertion complexes for the polymerization of olefins and/or dienes. The catalysts according to the invention can also be used as hydrogenation catalysts.

Suitable co-catalysts for polymerization processes include the co-catalysts which are known in the field of metallocene catalysis, such as polymeric or oligomeric aluminoxanes, Lewis acids, and aluminates and borates. In this connection, reference is made in particular to Macromol.

Symp. Vol. 97, July 1995, pages 1–246 (for alumoxanes) and to EP 277003, EP 277004, Organometallics 1997, 16. 842–857 (for borates), and to EP 573403 (for aluminates).

Co-catalysts which are particularly suitable include methylaluminoxane, methyl-alumoxane which is modified by triisobutylaluminum, diisobutylalumoxane, trialkylaluminum compounds such as trimethylaluminum, triethylaluminum, triisobutylaluminum or triisooctylaluminum, and also dialkylaluminum compounds such as diisobutylaluminum hydride, diisobutylaluminum fluoride and diethyl-aluminum chloride, substituted triarylaluminum compounds such as tris-(pentafluorophenyl) aluminum, ionic compounds which contain tetrakis-(pentafluorophenyl)aluminate as their anion, such as triphenylmethyl-tetrakis (penta-fluoro-phenyl)aluminate, as well as N,N-dimethylanilinium-tetrakis(pentafluoro-phenyl) aluminate, substituted triarylboron compounds such as tris-(pentafluoro-phenyl)boron, and ionic compounds which container tetrakis(pentafluorphenyl)borate as their anion, such as triphenylmethyl tetrakis-(pentafluorophenyl)borate, and N,N-dimethylanilinium tetrakis(pentafluorphenyl)-borate. Mixtures of different co-catalysts are also suitable for the activation of the catalysts according to the invention.

The term "polymerization" is to be understood here to mean both homo- and copolymerization of olefins and/or dienes. The following olefins in particular are used for polymerization: $C_2$–$C_{10}$ alkenes such as ethylene, propylene, butene-I, pentene-1 and hexene-I, octene-1, isobutylene, and arylalkenes such as styrene. The following are used in particular as dienes: conjugated dienes such as 1,3-butadiene, isoprene or 1,3-pentadiene, and unconjugated dienes such as 1,4-hexadiene, 1,5-heptadiene, 5,7-dimethyl-1,6-octadiene, 4-vinyl-1-cyclohexene, 5-ethylidene-2-norbornene, 5-vinyl-2-norbornene and dicyclopentadiene.

The catalysts according to the present invention are suitable for the production of polyethylene and of rubbers based on copolymers of ethylene with one or more of the aforementioned α-olefins and of the aforementioned dienes. The catalysts according to the invention are also suitable for the polymerization of cyclo-olefins such as norbornene, cyclopentene, cyclohexene and cyclooctene, and are suitable for the copolymerization of cycloolefins with ethylene or α-olefins.

Polymerization can be conducted in the liquid phase, in the presence or absence of an inert solvent, or in the gas phase. Suitable solvents include aromatic hydrocarbons such as benzene and/or toluene, or aliphatic hydrocarbons such as propane, hexane, heptane, octane, isobutane, cyclohexane or mixtures of different hydrocarbons.

It is possible to use the catalysts according to the invention to deposit on a support. Examples of suitable support materials include inorganic or organic polymeric supports, such as silica, zeolites, carbon black, activated carbon, alumina, polystyrene or polypropylene for example.

The catalysts according to the present invention can be deposited on support materials in the customary manner. Methods of supporting catalyst systems are described, for example, in U.S. Pat. Nos. 4,808,561, 4,912,075, 5,008,228 and 4,914,253.

Polymerization is generally conducted at pressures of 1 to 1000 bar, preferably 1 to 100 bar, and at temperatures of −100 to +250° C., preferably 0 to +150° C. Polymerization can be effected in customary reactors, either continuously or batch-wise.

For example, the (co)polymerization of ethylene with or without the aforementioned comonomers can be conducted as follows: after the customary preparation operations, a steel autoclave is filled with a solvent and with a scavenger, e.g., triisobutylaluminum or methylaluminoxane. Possible impurities and catalyst poisons, e.g., water or other oxygen-containing compounds, are rendered harmless by the scavenger. The reactor is subsequently filled with monomers up to a defined pressure, is thermostatted at a selected temperature, and polymerization is initiated by adding the pre-activated catalyst. Pre-activation can be effected, for example, by stirring a mixture of the catalyst with a co-catalyst, e.g., methylaluminoxane, in a defined quantitative ratio, in a solvent. Polymerization can be effected by a continuous or by a batch process.

The invention is explained in greater detail by means of the following examples.

General information: the preparation and handling of organometallic compounds were effected with the exclusion of air and moisture under a protective argon atmosphere (Schlenk technique). All the requisite solvents were rendered absolute before use by boiling for several hours over a suitable drying agent followed by distillation under argon. The compounds were characterized by $^1$H NMR, $^{13}$C NMR and mass spectrometry.

Polymer characterization: DSC measurements were made in an instrument supplied by Perkin-Elmer and termed a DSC-2 differential scanning calorimeter, according to the following procedure: two heating stages from −90° C., to +180° C., heating rate 20K/min, rapid cooling at 320K/min to −90° C., flushing with nitrogen; 12.3 mg of sample weighed into standard capsules. The polymer composition was determined by IR spectroscopy according to ASTM D 3900.

Abbreviations:

| | |
|---|---|
| THF | tetrahydrofuran |
| MS | mass spectrum |
| MAO | methylaluminoxane |
| dH | enthalpy of fusion (DSC measurement) |
| Tg | glass transition temperature (DSC measurement) |

The invention is further illustrated but is not intended to be limited by the following examples in which all parts and percentages are by weight unless otherwise specified.

EXAMPLE 1

Synthesis of compound 1 via reaction of 6,6-dimethylfulvene with TiCl$_4$.2 THF in the presence of magnesium and subsequent reaction with benzophenone

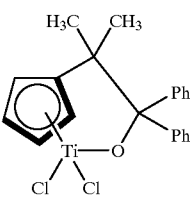

TiCl$_4$.2 THF (710 mg, 2.13 mmoles) and an equivalent amount of magnesium (52 mg, 2.13 mmoles) were placed in a vessel in 25 ml THF. 1.01 equivalents 6,6-dimethylfulvene (230 mg, 2.16 mmoles) were added drop-wise thereto at room temperature. The batch was left overnight at room temperature with stirring, so that all the magnesium was consumed. After the slow, drop-wise addition of a solution of benzophenone (0.387 g, 2.13 mmoles) in 5 ml THF, the batch was stirred for 2 hours at room temperature, the solvent was removed under high vacuum and the product was taken up in toluene. The solid was filtered off and the solution was concentrated to 10 ml. A red solid was precipitated by the addition of 20 ml hexane. The batch was cooled to −20° C. for further crystallization. The solid was isolated and was dried under high vacuum. 230 mg (27%) compound 1 as dark red solid were obtained, which was characterised by NMR and mass spectrometry.

$^1$H-NMR: (C$_6$D$_6$, 300 MHz): δ=0.92 (s, 6H, C(CH$_3$)$_2$), 5.79 (dd, 2H, $^2$J(H,H)=2.69 Hz, C$_5$H$_4$), 6.81 (dd, 2H, $^2$J(H,H)=2.69 Hz, C$_5$H$_4$), 7.03–7.26 (m, 6H, C$_6$H$_5$), 7.70–7.75 (m, 4H, C$_6$H$_5$) ppm.

$^{13}$C NMR: (C$_6$D$_6$, 75 MHz): δ=27.89 (C(CH$_3$)$_2$), 45.23 (C(CH$_3$)$_2$), 115.09/116.39/119.83/120.49 (C$_4$H$_4$), 112.74/128.53/130.33/132.31 (o,m,p-C$_6$H$_5$), 138.33 (ipso-C$_5$H$_4$), 144.45 (i-C$_6$H$_5$) ppm.

MS: (70 eV) m/e: 406 (2) [M$^+$], 372 (5) [M$^+$-HCl], 330 (30) [M$^+$-Ph], 224 (25) [M$^+$-OCPh$_2$], 182 (65) [OCPh$_2$], 105 (100) [6,6-dimethylfulvene], 77 (70) [Ph].

EXAMPLE 2

Polymerization of Ethylene 500 ml toluene and 1 ml of a 10% solution of MAO in toluene were placed in a 1.4 liter steel autoclave and were maintained at a controlled temperature of 25° C. Ethylene was then added until the reactor internal pressure rose to 6 bar. Pre-activation of the catalyst: a solution of 2.0 mg of compound 1 from Example 1 in 2.5 ml toluene was stirred for 10 minutes at room temperature with 2 ml of a 10% solution of MAO in toluene. Polymerization was initiated by adding the pre-activated catalyst solution (5 μmoles titanium). After a duration of polymerization of 30 minutes at 25° C. and 7 bar, the autoclave was depressurized, polymerization was stopped by adding a 1% HCl solution in methanol, and the batch was stirred for 1 hour. The polymer which was thus obtained was filtered off, washed with methanol, isolated and dried under vacuum for 20 hours at 60° C. 26.5 g of highly crystalline polyethylene were obtained. The DSC melting point during the 1st heating stage was 147.1° C. (dH=251.8 J/g), and the melting point during the 2nd heating stage was 135.9° C. (dH=144 J/g).

EXAMPLE 3
Copolymerization of Ethylene and 1-hexene 500 ml toluene, 20 ml hexene-1 and 1 ml of a 10% solution of MAO in toluene were placed in a 1.4 liter steel autoclave. This solution was maintained at a controlled temperature of 40° C. Ethylene was then added until the reactor internal pressure rose to 6 bar. Pre-activation of the catalyst: a solution of 4.0 mg of the product from Example 1 in 5 ml toluene was stirred for 10 minutes at room temperature with 5 ml of a 10% solution of MAO in toluene. Polymerization was initiated by adding the pre-activated catalyst solution (10 μmoles titanium). After a duration of polymerization of 60 minutes at 40° C. and 6 bar, the autoclave was depressurized, polymerization was stopped by adding a 1% solution of HCl in methanol, and the batch was stirred for 1 hour. The polymer which was thus obtained was filtered off, washed with methanol, isolated and dried under vacuum for 20 hours at 60° C. 22.2 g of an ethylene/1-hexene copolymer were obtained. The DSC melting point during the 2nd heating stage was 118° C. (dH=112.5 J/g). The DSC measurement gave a Tg of −20.5° C.

EXAMPLE 4
Synthesis of compound 2 via reaction of 2,3,4,5-tetramethylfulvene with $TiCl_4.2$ THF in the presence of magnesium, and subsequent reaction with benzophenone

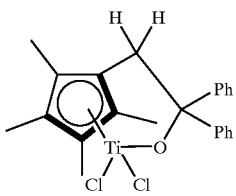

2

$TiCl_4.2$ THF (510 mg, 1.53 mmoles) and magnesium (37 mg, 1.53 mmoles) were placed in a vessel in 10 ml THF. 1.05 equivalents of 2,3,4,5-tetramethyl-fulvene (215 mg, 1.60 mmoles) were added drop-wise to this solution. The batch was left overnight with stirring so that the magnesium was completely consumed. Benzophenone (0.280 g, 1.53 mmoles) in 5 ml THF was added at room temperature. After 2 hours, the batch was evaporated to dryness under high vacuum, and the product was taken up in 30 ml hexane and was filtered free from magnesium chloride. Concentration of the batch to half its volume and subsequent crystallization at −20° C. gave 280 mg (42%) compound 2 as brownish red solid which was characterized by NMR and mass spectrometry.

$^1$H NMR: ($C_6D_6$, 300 MHz): δ=1.69 (s, 6H, $C_5(CH_3)_4$), 1.95 (s, 6H, $C_5(CH_3)_4$), 3.94 (s, 2H, —$CH_2$—) 6.91 (m, 4H $C_6H_5$), 7.13 (m, 4H, $C_6H_5$), 7.56 (m, 2H $C_6H_5$) ppm.

$^{13}$C NMR: ($C_6D_6$, 75 MHz): δ=13.05, 14.18 ($C_5(CH_3)_4$), 44.04 (—$CH_2$—), 124.67, 127.38, 128.97 (o,m,p-$C_6H_5$), 118.04, 128.88, 130.42 ($C_5(CH_3)_4$), 149.27 (i-$C_6H_5$) ppm.

MS: (70 eV) m/e: 434 (10) [M$^+$], 356 (5) [M$^+$-Ph], 332 (100) [M$^+$-2HCl-2CH$_3$], 316 (10) [M$^+$-TiCl$_2$], 252 (30) [M$^+$-OCPh$_2$], 182(35)[OCPh$_2$], 135 (25) [$C_5(CH_3)_4$=$CH_2$], 77 (65) [Ph].

EXAMPLE 5
Reaction of 6,6-dimethylfulvene with $TiCl_4.2$ THF in the Presence of Magnesium and Subsequent Reaction with 4-fluorophenyl Methyl Ketone 710 mg (2.13 mmoles) $TiCl_4.2$ THF and 51.4 mg (2.13 mmoles) magnesium were placed in a vessel in 25 ml THF. 0.26 ml (2.16 mmoles) 6,6-di-methylfulvene were added drop-wise to this solution at room temperature. The batch was left overnight with stirring, so that the magnesium was completely consumed. After the slow drop-wise addition of a solution of 294 mg (2.13 mmoles) 4-fluorophenyl methyl ketone in 5 ml THF and stirring for 2 hours, the batch was evaporated to dryness under high vacuum, and was taken up in 25 ml toluene and filtered free from magnesium chloride. Concentration to half the volume and subsequent crystallization at −20° C. gave 242 mg of a dark brown crystalline solid.

EXAMPLE 6
Polymerization of Ethylene 100 ml toluene and 5 ml of a 10% solution of methylalumoxane (MAO) were placed in a 250 ml glass reactor. Ethylene at a pressure of 1.1 bar was subsequently passed continuously into the solution through a gas inlet tube. Polymerization was initiated by adding a solution of 4.4 mg of the product from Example 5 in 5 ml toluene. The reaction, which proceeded at a temperature of 40° C. and at an ethylene pressure of 1.1 bar, was stopped after a duration of polymerization of 10 minutes by adding 10 ml methanol, and the resulting polymer was filtered off, washed with methanol and dried in a vacuum drying oven. 0.96 g polyethylene was obtained.

EXAMPLE 7
Reaction of 6,6-dimethylfulvene with $TiCl_4.2$ THF in the Presence of Magnesium, and Subsequent Reaction with 3,3-dimethyl-2-butanone 384.8 mg (1.15 mmoles) $TiCl_4.2$ THF and 28 mg (1.15 mmoles) magnesium were placed in a vessel in 15 ml THF. 0.14 ml (1.16 mmoles) 6,6-di-methylfulvene were added drop-wise at room temperature to this solution. The batch was left overnight with stirring, so that the magnesium was completely consumed. After the slow, drop-wise addition of a solution of 15 mg (1.15 mmoles) 3,3-dimethyl-2-butanone in 2.5 ml THF, and after stirring for 2 hours, the batch was evaporated to dryness under high vacuum, and the residue was taken up in 28.8 ml toluene. A suspension was obtained which had a content of 40 μmoles titanium/ml.

EXAMPLE 8
Polymerization of Ethylene

The polymerization procedure of Example 6 was repeated, except that the suspension from Example 7 was used as the catalyst instead of the product from Example 5. Polymerization was initiated by adding 0.25 ml of the suspension from Example 7 (10 μmoles titanium). 1.71 g polyethylene was obtained.

EXAMPLE 9
Reaction of 6,6-diphenylfulvene with $TiCl_4.2$ THF in the Presence of Magnesium, and Subsequent Reaction with 3,3-dimethyl-2-butanone 710 mg (2.13 mmoles) $TiCl_4.2$ THF and 51.4 mg (2.13 mmoles) magnesium were placed in a vessel in 20 ml THF. 490.6 mg (2.13 mmoles) 6,6-diphenylfulvene were added to this solution at room temperature. The batch was left overnight with stirring, so that the magnesium was completely consumed. After the slow, drop-wise addition of a solution of 213 mg (2.13 mmoles) 3,3-dimethyl-2-butanone in 5 ml THF, and after stirring for 2 hours, the batch was evaporated to dryness under high vacuum and the residue was taken up in 25 ml toluene. A suspension was obtained which had a content of 42.6 μmoles titanium/ml.

EXAMPLE 10
Polymerization of Ethylene 90 ml n-hexane, 0.5 ml of a 2 molar solution of trimethylaluminum in toluene, and a solution of 18.4 mg (20 μmoles) $CPh_3[B(C_6F_5)_4]$ in 10 ml toluene were placed in a glass reactor. Ethylene at a pressure of 1.1 bar was subsequently passed continuously into the solution through a gas inlet tube. Polymerization was initiated by adding 0.23 ml of the suspension from Example 9 (10 μmoles titanium). The reaction, which proceeded at a temperature of 40° C. and at an ethylene pressure of 1.1 bar, was stopped after a duration of polymerization of 15 minutes by adding methanol, and the resulting polymer was filtered off, washed with acetone and dried in a vacuum drying oven. 2.14 g polyethylene were obtained.

EXAMPLE 11
Polymerization of Ethylene 500 ml n-hexane and 5 ml of a 10% solution of MAO in toluene were placed in a 1.4 liter steel autoclave and were maintained at a controlled temperature of 40° C. Ethylene was then metered in until the reactor internal pressure rose to 6 bar. Pre-activation of the catalyst: 0.23 ml of the suspension from Example 9 was stirred for 10 minutes at room temperature with 5 ml of a 10% solution of MAO in toluene. Polymerization was initiated by adding the pre-activated catalyst solution (10 μmoles titanium). After a duration of polymerization of 10 minutes at 40° C. and 6 bar, the autoclave was depressurized. Polymerization was stopped by adding a solution of 1% HCl in methanol and the batch was stirred for 1 hour. The polymer which was thus obtained was filtered off, washed with methanol, isolated and dried for 20 hours at 60° C. under vacuum. 13.6 g of highly crystalline polyethylene was obtained. The DSC melting point during the 1st heating stage was 145.4° C. (dH=215 J/g), and during the 2nd heating stage was 135.9° C. (dH=138 J/g).

EXAMPLE 12
Copolymerization of Ethylene and Propylene 500 ml hexane and 5 ml of a 10% solution of MAO in toluene were placed in a 1.4 liter steel autoclave which was fitted with a mechanical stirrer, a manometer, a temperature sensor, a temperature controller, a catalyst lock and a monomer metering device for ethylene and propylene. The internal temperature was set to 40° C. by a thermostat. 14 g ethylene and 28.3 g propylene were subsequently metered in. Pre-activation of the catalyst: 0.23 ml of the suspension from Example 9 was stirred for 10 minutes at room temperature with 5 ml of a 10% solution of MAO in toluene. Polymerization was initiated by adding the pre-activated catalyst solution (10 μmoles titanium). Using a semi-batch procedure, ethylene and propylene were continuously metered in at a ratio by weight of 3:7 so that the internal pressure at 40° C. remained constant at 5 bar. After a duration of polymerization of 40 minutes, polymerization was stopped by adding a solution of 1% HCl in methanol, and the batch was stirred for 1 hour. The polymer which was thus obtained was filtered off, washed with methanol, isolated and dried for 20 hours at 60° C. under vacuum, whereupon 49.8 g copolymer were obtained. A Tg of −54° C. (2nd heating) was determined by the DSC method.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of producing metal fulvene insertion complexes, comprising the step of reacting a) a metal fulvene complex of formula (I)

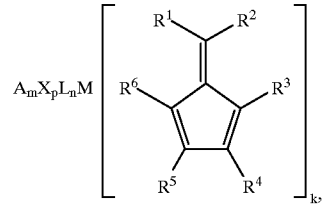

(I)

wherein

M is a metal of Groups IIIb, IVb, Vb, VIb or of the lanthanides or of the actinides of the IUPAC periodic table of the elements, A is an anionic ligand which is optionally singly- or multiply-bridged, with the exception of cyclopentadienyl ligands, X denotes a hydrogen atom, a $C_1$ to $C_{10}$ alkyl group, a $C_1$ to $C_{10}$ alkoxy group, a $C_6$ to $C_{10}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a silyl group substituted by $C_1$ to $C_{10}$ hydrocarbon radicals, a halogen atom or an amide of formula $NR^7_2$, L denotes a neutral ligand, $R^1$, $R^2$, $R^3$, $R^4$, $R^5$, $R^6$ are the same or different and represent hydrogen, a halogen, a cyano group, a $C_1$ to $C_{20}$ alkyl group, a $C_1$ to $C_{10}$ fluoroalkyl group, a $C_6$ to $C_{10}$ fluoroaryl group, a $C_1$ to $C_{10}$ alkoxy group, a $C_6$ to $C_{20}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkynyl group, a silyl group substituted by $C_1$–$C_{10}$ hydrocarbon radicals, a sulphide group substituted by a $C_1$–$C_{10}$ hydrocarbon radical, or an amino group which is optionally substituted by $C_1$–$C_{20}$ hydrocarbon radicals, or $R^1$, $R^2$, $R^3$, $R^4$, $R^5$, $R^6$ each form one or more aliphatic or aromatic ring systems together with the atoms which bond them, which ring systems may contain one or more hetero atoms (O, N, S) and comprise 5 to 10 carbon atoms, $R^7$ represents hydrogen, a $C_1$ to $C_{20}$ alkyl group, a $C_6$ to $C_{20}$ aryl group, a $C_7$ to $C_{40}$ arylalkyl group, a $C_7$ to $C_{40}$ alkylaryl group, a silyl group which is substituted by $C_1$–$C_{10}$ hydrocarbon radicals, or an amino group which is optionally substituted by $C_1$–$C_{20}$ hydrocarbon radicals, m, p represent the numbers 0, 1, 2, 3 or 4 which result from the valency and the state of bonding of M, k represents the number 1, 2 or 3, and the sum of k+m+p ranges from 1 to 5 depending on the oxidation state of M, and n is a number from 0 to 10, with b) an unsaturated compound of formula (II)

$R^8{}_a R^9{}_b CY$  (II), wherein

R[8] and R[9] are the same or different, and denote a hydrogen atom, a halogen atom, a hydroxy group, a $C_1$ to $C_{10}$ alkyl group, a $C_1$ to $C_{10}$ alkoxy group, a $C_6$ to $C_{10}$ aryl group which is optionally substituted by halogen atoms, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, an amino group which is optionally substituted by $C_1$–$C_{20}$ hydrocarbon radicals, or an imino group which is optionally substituted by $C_1$–$C_{20}$ hydrocarbon radicals, Y denotes a nitrogen atom, an oxygen atom, a sulphur atom or a group of formula $NR^{10}$, wherein $R^{10}$ has the same meaning as R[8] and R[9], and a and b represent the numbers 0 or 1.

2. A method according to claim 1, wherein

M denotes Ti, Zr or Hf,

X denotes a halogen,

L denotes diethyl ether or THF, p denotes the number 2, k denotes the number 1, m is zero, and n is an integer within the range from 0 to 4.

3. A method according to claim 1, wherein

Y denotes oxygen or nitrogen,

R[8] and R[9] denote hydrogen and/or a $C_1$–$C_{10}$ alkyl.

4. A metal fulvene insertion complex produced by reacting a) a metal fulvene complex of formula (I)

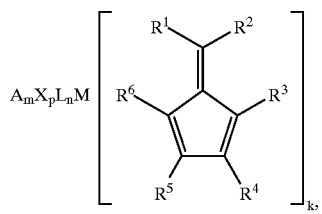

(I)

wherein

M is a metal of Groups IIIb, IVb, Vb, VIb or of the lanthanides or of the actinides of the IUPAC periodic table of the elements, A is an anionic ligand which is optionally singly- or multiply-bridged, with the exception of cyclopentadienyl ligands, X denotes a hydrogen atom, a $C_1$ to $C_{10}$ alkyl group, a $C_1$ to $C_{10}$ alkoxy group, a $C_6$ to $C_{10}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a silyl group substituted by $C_1$ to $C_{10}$ hydrocarbon radicals, a halogen atom or an amide of formula $NR^7_2$, L denotes a neutral ligand, R[1], R[2], R[3], R[4], R[5], R[6] are the same or different and represent hydrogen, a halogen, a cyano group, a $C_1$ to $C_{20}$ alkyl group, a $C_1$ to $C_{10}$ fluoroalkyl group, a $C_6$ to $C_{10}$ fluoroaryl group, a $C_1$ to $C_{10}$ alkoxy group, a $C_6$ to $C_{20}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkynyl group, a silyl group substituted by $C_1$–$C_{10}$ hydrocarbon radicals, a sulphide group substituted by a $C_1$–$C_{10}$ hydrocarbon radical, or an amino group which is optionally substituted by $C_1$–$C_{20}$ hydrocarbon radicals, or R[1], R[2], R[3], R[4], R[5], R[6] each form one or more aliphatic or aromatic ring systems together with the atoms which bond them, which ring systems may contain one or more hetero atoms (O, N, S) and comprise 5 to 10 carbon atoms, R[7] represents hydrogen, a $C_1$ to $C_{20}$ alkyl group, a $C_6$ to $C_{20}$ aryl group, a $C_7$ to $C_{40}$ arylalkyl group, a $C_7$ to $C_{40}$ alkylaryl group, a silyl group which is substituted by $C_1$–$C_{10}$ hydrocarbon radicals, or an amino group which is optionally substituted by $C_1$–$C_{20}$ hydrocarbon radicals, m, p represent the numbers 0, 1, 2, 3 or 4 which result from the valency and the state of bonding of M, k represents the number 1, 2 or 3, and the sum of k+m+p ranges from 1 to 5 depending on the oxidation state of M, and n is a number from 0 to 10, with b) an unsaturated compound of formula (II)

wherein

R[8] and R[9] are the same or different, and denote a hydrogen atom, a halogen atom, a hydroxy group, a $C_1$ to $C_{10}$ alkyl group, a $C_1$ to $C_{10}$ alkoxy group, a $C_6$ to $C_{10}$ aryl group which is optionally substituted by halogen atoms, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, an amino group which is optionally substituted by $C_1$–$C_{20}$ hydrocarbon radicals, or an imino group which is optionally substituted by $C_1$–$C_{20}$ hydrocarbon radicals, Y denotes a nitrogen atom or the group NH;

a and b represent the numbers 0 or 1.

5. A method according to claim 1, wherein said fulvene metal complexes of formula (I) are produced by the reaction of a transition metal compound of formula (III)

wherein

A, X, L, M, m and n have the same meaning as in claim 1 a and s denotes the number 2, 3, 4, 5 or 6 and s>p, with a fulvene compound of formula (IV)

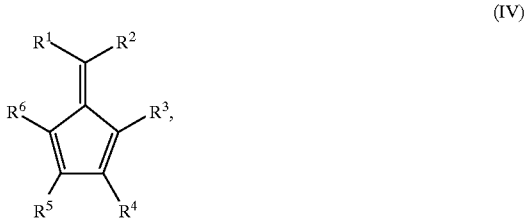

wherein

R[1], R[2], R[3], R[4], R[5] and R[6] have the same meaning as in claim 1, in the presence of a reducing agent.

6. A method according to claim 5, wherein

M denotes Ti, Zr or Hf,

X denotes a halogen,

L denotes diethyl ether or THF, m represents the number 0 s denotes the numbers 2, 3 or 4, and n is an integer within the range from 0 to 4.

7. A method according to claim 5, wherein said fulvene compound is selected from the group consisting of 6-cyclohexylfulvene, 6-isopropylfulvene, 6-tert-butyl fulvene, 6-phenyl-fulvene, 6-(dimethylamino)fulvene, 6,6-bis(dimethylamino)fulvene, 6,6-dimethylfulvene, 6,6-bis-(trifluoromethyl)fulvene, 6,6-diphenylfulvene, 6,6-bis (pentafluorophenyl)fulvene, 6,6-pentamethylene-fulvene, 6,6-tetramethylene-fulvene, 6,6-trimethylene-fulvene, 2-(2,4-cyclopentadien-1-ylidene)-1,3-dithiolane, 5-benzylidene-1,2,3-triphenyl-1,3-cyclo-pentadiene, 1,2,3,4-tetramethyl-fulvene, 1,2,3,4-tetraphenylfulvene, 2,3-dimethylfulvene, 2,3-diisopropylfulvene, 2,3-diphenylfulvene, 1,4-dimethyl-2,3-diphenylfulvene or 1,4-diethyl-2,3-diphenylfulvene.

8. A catalyst system comprising a metal fulvene insertion complex in combination with optionally, a cocatalyst, said metal fulvene insertion complex produced by reacting a) a metal fulvene complex of formula (I)

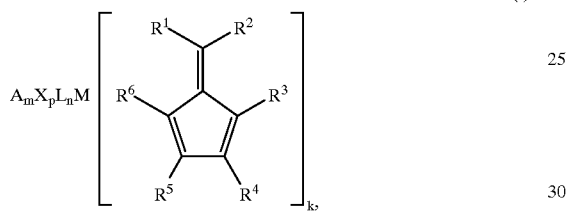

(I)

wherein

M is a metal of Groups IIIb, IVb, Vb, VIb or of the lanthanides or of the actinides of the IUPAC periodic table of the elements, A is an anionic ligand which is optionally singly- or multiply-bridged, with the exception of cyclopentadienyl ligands, X denotes a hydrogen atom, a $C_1$ to $C_{10}$ alkyl group, a $C_1$ to $C_{10}$ alkoxy group, a $C_6$ to $C_{10}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a silyl group substituted by $C_1$ to $C_{10}$ hydrocarbon radicals, a halogen atom or an amide of formula $NR^7{}_2$, L denotes a neutral ligand, $R^1$, $R^2$, $R^3$, $R^4$, $R^5$, $R^6$ are the same or different and represent hydrogen, a halogen, a cyano group, a $C_1$ to $C_{20}$ alkyl group, a $C_1$ to $C_{10}$ fluoroalkyl group, a $C_6$ to $C_{10}$ fluoroaryl group, a $C_1$ to $C_{10}$ alkoxy group, a $G_6$ to $C_{20}$ aryl group, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, a $C_2$ to $C_{10}$ alkynyl group, a silyl group substituted by $C_1$–$C_{10}$ hydrocarbon radicals, a sulphide group substituted by a $C_1$–$C_{10}$ hydrocarbon radical, or an amino group which is optionally substituted by $C_1$–$C_{20}$ hydrocarbon radicals, or $R^1$, $R^2$, $R^3$, $R^4$, $R^5$, $R^6$ each form one or more aliphatic or aromatic ring systems together with the atoms which bond them, which ring systems may contain one or more hetero atoms (O, N, S) and comprise 5 to 10 carbon atoms, $R^7$ represents hydrogen, a $C_1$ to $C_{20}$ alkyl group, a $C_6$ to $C_{20}$ aryl group, a $C_7$ to $C_{40}$ arylalkyl group, a $C_7$ to $C_{40}$ alkylaryl group, a silyl group which is substituted by $C_1$–$C_{10}$ hydrocarbon radicals, or an amino group which is optionally substituted by $C_1$–$C_{20}$ hydrocarbon radicals, m, p represent the numbers 0, 1, 2, 3 or 4 which result from the valency and the state of bonding of M, k represents the number 1, 2 or 3, and the sum of k+m+p ranges from 1 to 5 depending on the oxidation state of M, and n is a number from 0 to 10, with b) an unsaturated compound of formula (II)

(II)

wherein $R^8$ and $R^9$ are the same or different, and denote a hydrogen atom, a halogen atom, a hydroxy group, a $C_1$ to $C_{10}$ alkyl group, a $C_1$ to $C_{10}$ alkoxy group, a $C_6$ to $C_{10}$ aryl group which is optionally substituted by halogen atoms, a $C_6$ to $C_{10}$ aryloxy group, a $C_2$ to $C_{10}$ alkenyl group, a $C_7$ to $C_{40}$ arylalkyl group, a $C_7$ to $C_{40}$ alkylaryl group, a $C_8$ to $C_{40}$ arylalkenyl group, an amino group which is optionally substituted by $C_1$–$C_{20}$ hydrocarbon radicals, or an imino group which is optionally substituted by $C_1$–$C_{20}$ hydrocarbon radicals, Y denotes a nitrogen atom, or the group NH, a and b represent the numbers 0 or 1.

* * * * *